(12) United States Patent
Evans

(10) Patent No.: US 10,828,117 B2
(45) Date of Patent: Nov. 10, 2020

(54) CONSTANT FORCE SPRING ASSEMBLIES FOR ROBOTIC SURGICAL TOOLS

(71) Applicant: Ethicon LLC, Guaynabo, PR (US)

(72) Inventor: John Evans, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 451 days.

(21) Appl. No.: 15/794,581

(22) Filed: Oct. 26, 2017

(65) Prior Publication Data
US 2019/0125467 A1    May 2, 2019

(51) Int. Cl.
*A61B 34/00* (2016.01)
*A61B 34/30* (2016.01)
(Continued)

(52) U.S. Cl.
CPC ............. *A61B 34/71* (2016.02); *A61B 34/30* (2016.02); *A61B 34/37* (2016.02); *B25J 9/1689* (2013.01); *A61B 17/00234* (2013.01); *A61B 2017/00115* (2013.01); *A61B 2017/00199* (2013.01); *A61B 2017/00225* (2013.01); *A61B 2017/00398* (2013.01); *A61B 2017/00477* (2013.01); *A61B 2017/00876* (2013.01); *A61B 2034/302* (2016.02); *A61B 2034/305* (2016.02);
(Continued)

(58) Field of Classification Search
CPC ......... A61B 34/71; A61B 34/30; A61B 34/37; A61B 2034/302; A61B 2034/305; A61B 2034/715; A61B 2090/0808; A61B 2090/0811; A61B 2090/506; A61B 17/00234; A61B 2017/00115; A61B 2017/00199; A61B 2017/00225; A61B 2017/00398; A61B 2017/00477; A61B 2017/00876; B25J 9/1689
USPC ........................................................... 606/1
See application file for complete search history.

(56) References Cited

U.S. PATENT DOCUMENTS

| 8,831,782 | B2 | 9/2014 | Itkowitz |
| 2010/0082041 | A1 | 4/2010 | Prisco |

(Continued)

FOREIGN PATENT DOCUMENTS

| EP | 3112097 B1 | 1/2017 |
| WO | 2014/151621 | 9/2014 |

(Continued)

OTHER PUBLICATIONS

ISRWO of corresponding PCT/US2018/056402 dated Mar. 1, 2019.

*Primary Examiner* — Aaron F Roane
(74) *Attorney, Agent, or Firm* — Vorys, Sater, Seymour and Pease LLP

(57) ABSTRACT

A surgical tool includes a drive housing having an input shaft and a drive cable capstan arranged within the drive housing. The input shaft includes a drive gear and the drive cable capstan includes a driven gear intermeshed with the drive gear such that rotation of the input shaft rotates the drive cable capstan. An elongate shaft extends from the drive housing, and an end effector is operatively coupled to a distal end of the elongate shaft. A drive cable is coupled to the drive cable capstan and extends to the end effector. A spring assembly includes a winder drum and a constant force spring extending between the winder drum and the input shaft. The constant force spring provides a constant torque force that resists rotation of the input shaft and thereby prevents the drive cable from slackening.

20 Claims, 9 Drawing Sheets

(51) Int. Cl.
  *A61B 34/37*  (2016.01)
  *B25J 9/16*   (2006.01)
  *A61B 90/00*     (2016.01)
  *A61B 90/50*     (2016.01)
  *A61B 17/00*     (2006.01)

(52) U.S. Cl.
  CPC . *A61B 2034/715* (2016.02); *A61B 2090/0808* (2016.02); *A61B 2090/0811* (2016.02); *A61B 2090/506* (2016.02)

(56) References Cited

U.S. PATENT DOCUMENTS

| 2010/0331820 | A1  | 12/2010 | Pasco |
| 2012/0123441 | A1* | 5/2012  | Au ......................... A61B 34/30 |
|              |     |         | 606/130 |
| 2015/0313676 | A1  | 11/2015 | Deodhar |
| 2016/0287252 | A1  | 10/2016 | Parihar |

FOREIGN PATENT DOCUMENTS

| WO | 2014/151952   | 9/2014 |
| WO | 2015142786 A1 | 9/2015 |

* cited by examiner

CONSTANT FORCE SPRING ASSEMBLIES FOR ROBOTIC SURGICAL TOOLS

BACKGROUND

Minimally invasive surgical (MIS) instruments are often preferred over traditional open surgical devices due to reduced post-operative recovery time and minimal scarring. Endoscopic surgery is one type of MIS procedure in which an elongate flexible shaft is introduced into the body of a patient through a natural orifice. Laparoscopic surgery is another type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The trocar also helps facilitate insufflation to elevate the abdominal wall above the organs. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more intuitive hand movements by maintaining natural eye-hand axis. Robotic systems can also allow for more degrees of freedom in movement by including a "wrist" joint that creates a more natural hand-like articulation. The instrument's end effector can be articulated (moved) using a cable driven motion system having one or more drive cables that extend through the wrist joint.

Minimally invasive surgical (MIS) instruments are often preferred over traditional open surgical devices due to reduced post-operative recovery time and minimal scarring. Endoscopic surgery is one type of MIS procedure in which an elongate flexible shaft is introduced into the body of a patient through a natural orifice. Laparoscopic surgery is another type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The trocar also helps facilitate insufflation to elevate the abdominal wall above the organs. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more intuitive hand movements by maintaining natural eye-hand axis. Robotic systems can also allow for more degrees of freedom in movement by including a "wrist" joint that creates a more natural hand-like articulation. The instrument's end effector can be articulated (moved) using a cable driven motion system having one or more drive cables that extend through the wrist joint.

A user (e.g., a surgeon) is able to remotely operate an instrument's end effector by grasping and manipulating in space one or more controllers that communicate with a tool driver coupled to the surgical instrument. User inputs are processed by a computer system incorporated into the robotic surgical system and the tool driver responds by actuating the cable driven motion system and, more particularly, the drive cables. Moving the drive cables articulates the end effector to desired positions and configurations. A number of mechanical and manufacturing hurdles must be overcome through component design and assembly to enable consistent and predictable performance of the end effector and its associated cable driven motion system.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to robotic surgical systems and, more particularly, to improved cable driven motion systems having a constant force spring assembly that provides constant torque resistance to prevent drive cables from slackening.

Embodiments discussed herein describe constant force spring assemblies that help maintain a minimum level of force on drive cables included in robotic surgical systems, and thereby prevents the drive cables from relaxing. The constant force spring assemblies provide a simple spool-to-spool take up that results in a constant torque resistance being applied to the drive cables. In contrast to conventional torsion springs that increase resistance with displacement, the torque resistance stays constant with the presently described constant force spring assemblies. An example, constant force spring assembly includes a winder drum and a constant force spring extending between the winder drum and an input shaft. The constant force spring provides a constant torque force that resists rotation of the input shaft and thereby prevents a drive cable that moves based on rotation of the input shaft from slackening.

FIGS. 1-5 illustrate the structure and operation of example robotic surgical systems and components thereof.

Figure 1:
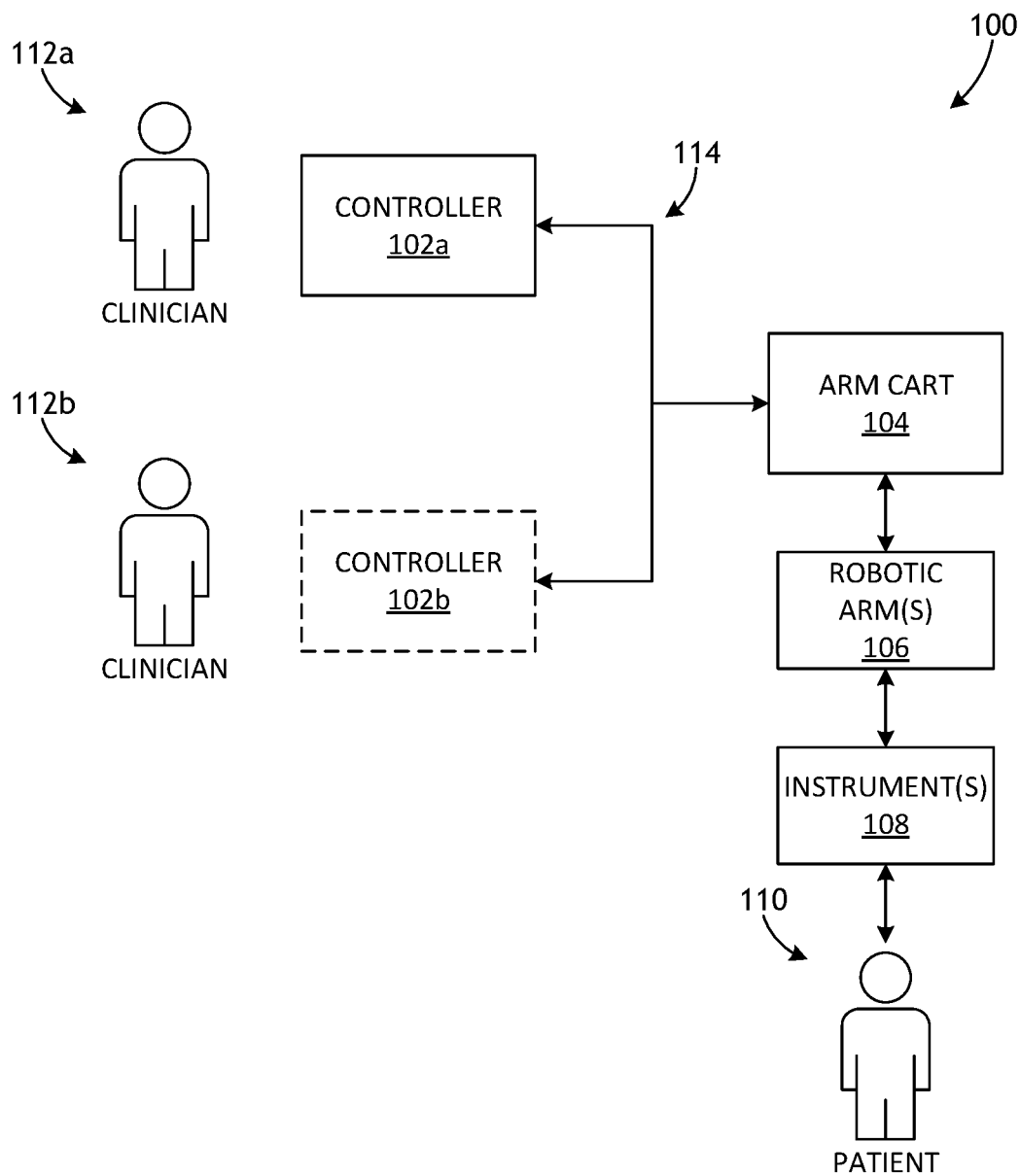
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one master controller 102a and at least one arm cart 104. The arm cart 104 may be mechanically and/or electrically coupled to one or more robotic arms 106, alternately referred to as "tool drivers". Each robotic arm 106 may include and otherwise mount one or more surgical tools or instruments 108 for performing various surgical tasks on a patient 110. Operation of the arm cart 104, including the arms 106 and instruments 108 may be directed by a clinician 112a (e.g., a surgeon) from the master controller 102a.

In some embodiments, a second master controller 102b (shown in dashed lines) operated by a second clinician 112b may also direct operation of the arm cart 104 in conjunction with the first clinician 112a. In such embodiments, for example, each clinician 122a,b may control different arms 106 of the arm cart 104 or, in some cases, complete control of the arm cart 104 may be passed between the clinicians 112a,b. In some embodiments, additional arm carts (not shown) may be utilized on the patient 110, and these additional arm carts may be controlled by one or more of the master controllers 102a,b.

The arm cart(s) 104 and the master controllers 102a,b may be in communication with one another via a communications link 114, which may be any type of wired or wireless communications link configured to carry suitable types of signals (e.g., electrical, optical, infrared, etc.) according to any communications protocol. The communications link 114 may be an actual physical link or it may be a logical link that uses one or more actual physical links. When the link is a logical link the type of physical link may be a data link, uplink, downlink, fiber optic link, point-to-point link, for example, as is well known in the computer networking art to refer to the communications facilities that connect nodes of a network. Example implementations of robotic surgical systems, such as the system 100, are disclosed in U.S. Pat. No. 7,524,320, the contents of which are incorporated herein by reference. The various particularities of such devices will not be described in detail herein beyond that which may be necessary to understand various embodiments and forms of the various embodiments of robotic surgery apparatus, systems, and methods disclosed herein.

Figure 2:
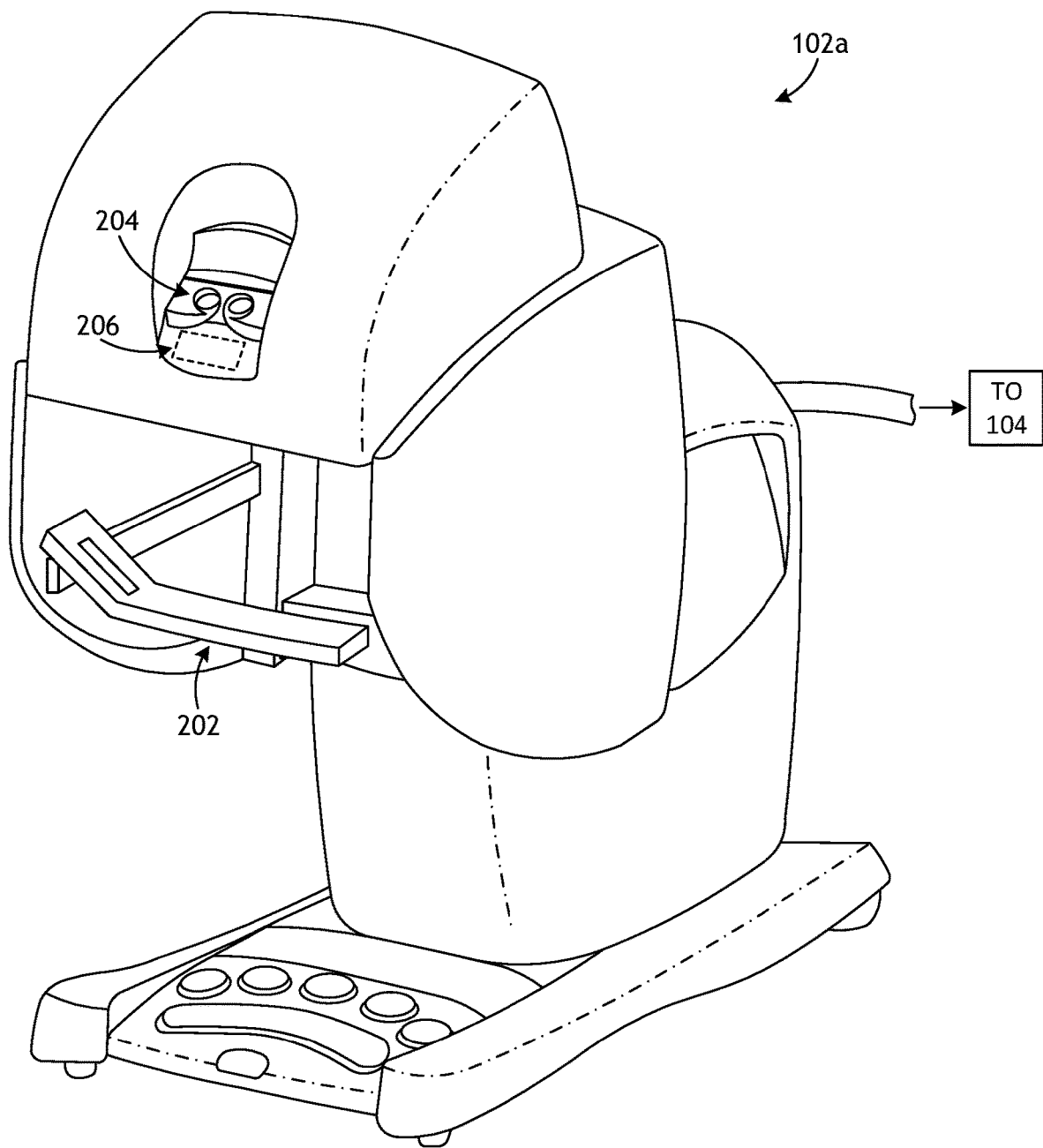
FIG. 2 is an example embodiment of the master controller of FIG. 1 that may be used to operate a robotic arm slave cart.

FIG. 2 is an example embodiment of the master controller 102a that may be used to operate a robotic arm slave cart, such as the arm cart 104 of FIG. 1. The master controller 102a and its associated arm cart 104, as well as their respective components and control systems, are collectively referred to herein as a "robotic surgical system." Examples of such systems and devices are disclosed in U.S. Pat. No. 7,524,320 and, therefore, will not be described in detail herein beyond that which may be necessary to understand various embodiments and forms of the present invention.

The master controller 102a generally includes one or more controllers 202 that can be grasped by a surgeon (e.g., the clinician 112a of FIG. 1) and manipulated in space while the surgeon views the procedure via a stereo display 204. The master controllers 202 generally comprise manual input devices designed to move in multiple degrees of freedom, and which often further have an actuatable handle for actuating a surgical instrument (e.g., the surgical instrument(s) 108 of FIG. 1), for example, for opening and closing opposing jaws, applying an electrical potential to an electrode, or the like.

In the illustrated example, the master controller 102a further includes an optional feedback meter 206 viewable by the surgeon via the display 204 to provide the surgeon with a visual indication of the amount of force being applied to the surgical instrument (i.e., a cutting instrument or dynamic clamping member). Other sensor arrangements may be employed to provide the master controller 102a with an indication of other surgical instrument metrics, such as whether a staple cartridge has been loaded into an end effector or whether an anvil has been moved to a closed position prior to firing, for example.

Figure 3:
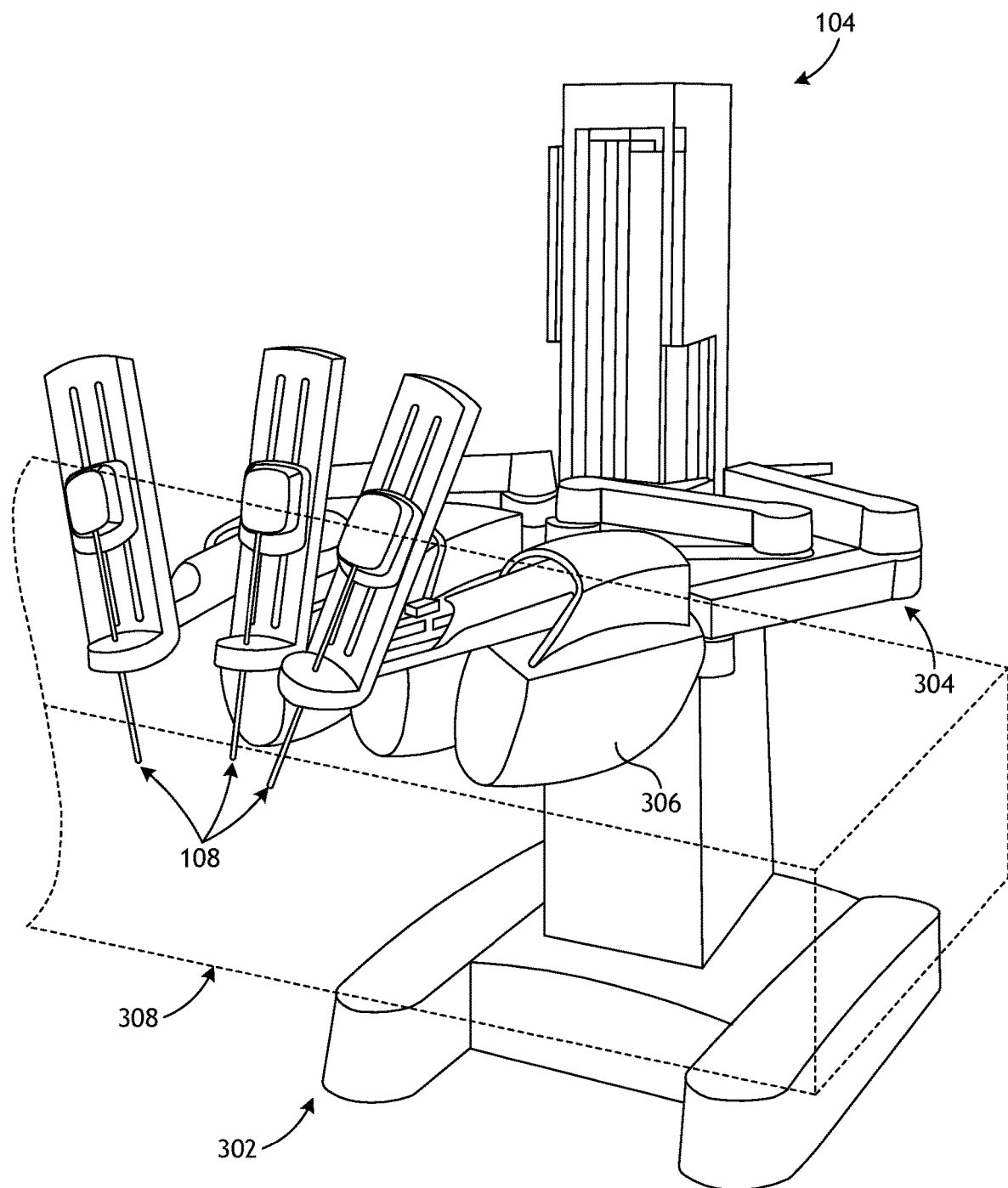
FIG. 3 depicts an example embodiment of the robotic arm cart of FIG. 1 used to actuate a plurality of surgical instruments.

FIG. 3 depicts an example embodiment of the robotic arm cart 104 used to actuate a plurality of surgical instruments 108, alternately referred to as "surgical tools." Various robotic surgery systems and methods employing master controller and robotic arm cart arrangements are described in U.S. Pat. No. 6,132,368, the contents of which are hereby incorporated by reference. As illustrated, the robotic arm cart 104 may include a base 302 that supports three surgical instruments 108, and the surgical instruments 108 are each supported by a series of manually articulatable linkages, generally referred to as set-up joints 304, and a robotic manipulator 306. These structures are herein illustrated with protective covers extending over much of the robotic linkage. These protective covers may be optional, and may be limited in size or entirely eliminated in some embodiments to minimize the inertia that is encountered by the servo mechanisms used to manipulate such devices, to limit the volume of moving components so as to avoid collisions, and to limit the overall weight of the cart 104.

The cart 104 will generally have dimensions suitable for transporting the cart 104 between operating rooms. The cart 104 may be configured to typically fit through standard operating room doors and onto standard hospital elevators. In some embodiments, the cart 104 may include a wheel system (or other transportation system) that allows the cart 104 to be positioned adjacent an operating table by a single attendant. In various embodiments, an automated reloading system including a base portion may be strategically located within a work envelope 308 of the robotic arm cart 104.

Figure 4:
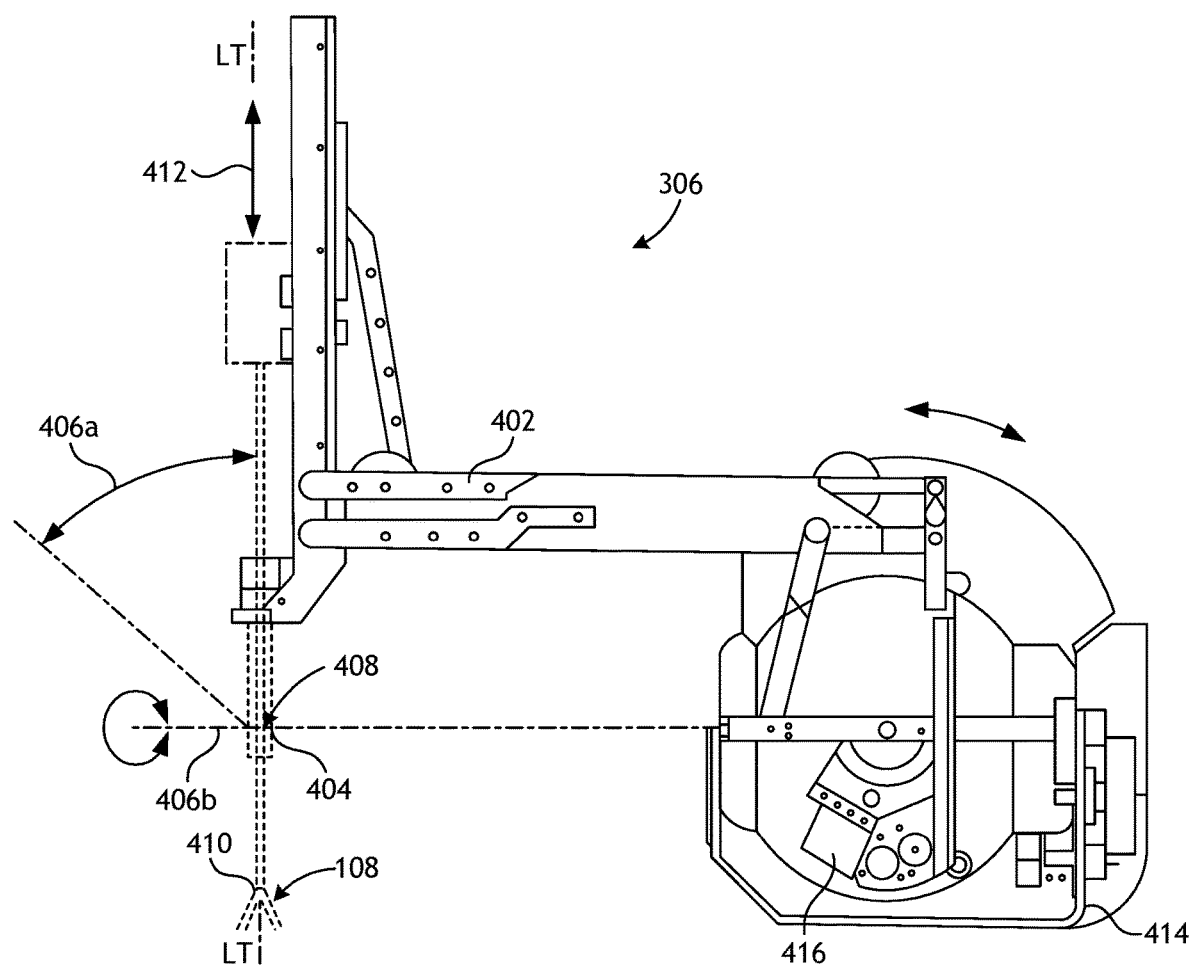
FIG. 4 is a side view schematic diagram of an example embodiment of the robotic manipulator of FIG. 3.

FIG. 4 is a side view schematic diagram of an example embodiment of the robotic manipulator 306. As illustrated, the robotic manipulator 306 may include linkage 402 that constrains movement of the surgical instrument 108 coupled thereto. The linkage 402 includes rigid links coupled by rotational joints in a parallelogram arrangement so that the surgical instrument 108 rotates around a point 404 in space.

The parallelogram arrangement constrains rotation to pivoting about a first axis 406a, referred to as the "pitch axis." The links supporting the parallelogram linkage 402 are pivotally mounted to set-up joints 304 (FIG. 3) so that the surgical instrument 108 further rotates about a second axis 406b, referred to as the "yaw axis." The pitch and yaw axes 406a, 406b intersect at a remote center 408, which is aligned along a shaft 410 of the surgical instrument 108.

The surgical instrument 108 may have further degrees of driven freedom as supported by the robotic manipulator 306, including sliding motion of the surgical instrument 108 along a longitudinal tool axis "LT-LT". As the surgical instrument 108 slides (translates) along the longitudinal tool axis LT-LT relative to the robotic manipulator 306 (arrow 412), the remote center 408 remains fixed relative to a base 414 of the robotic manipulator 306. Hence, the entire robotic manipulator 306 is generally moved to re-position the remote center 408.

The linkage 402 of the robotic manipulator 306 is driven by a series of motors 416. These motors 416 actively move the linkage 402 in response to commands from a processor of a control system. The motors 416 may also be employed to manipulate the surgical instrument 108.

Figure 5:
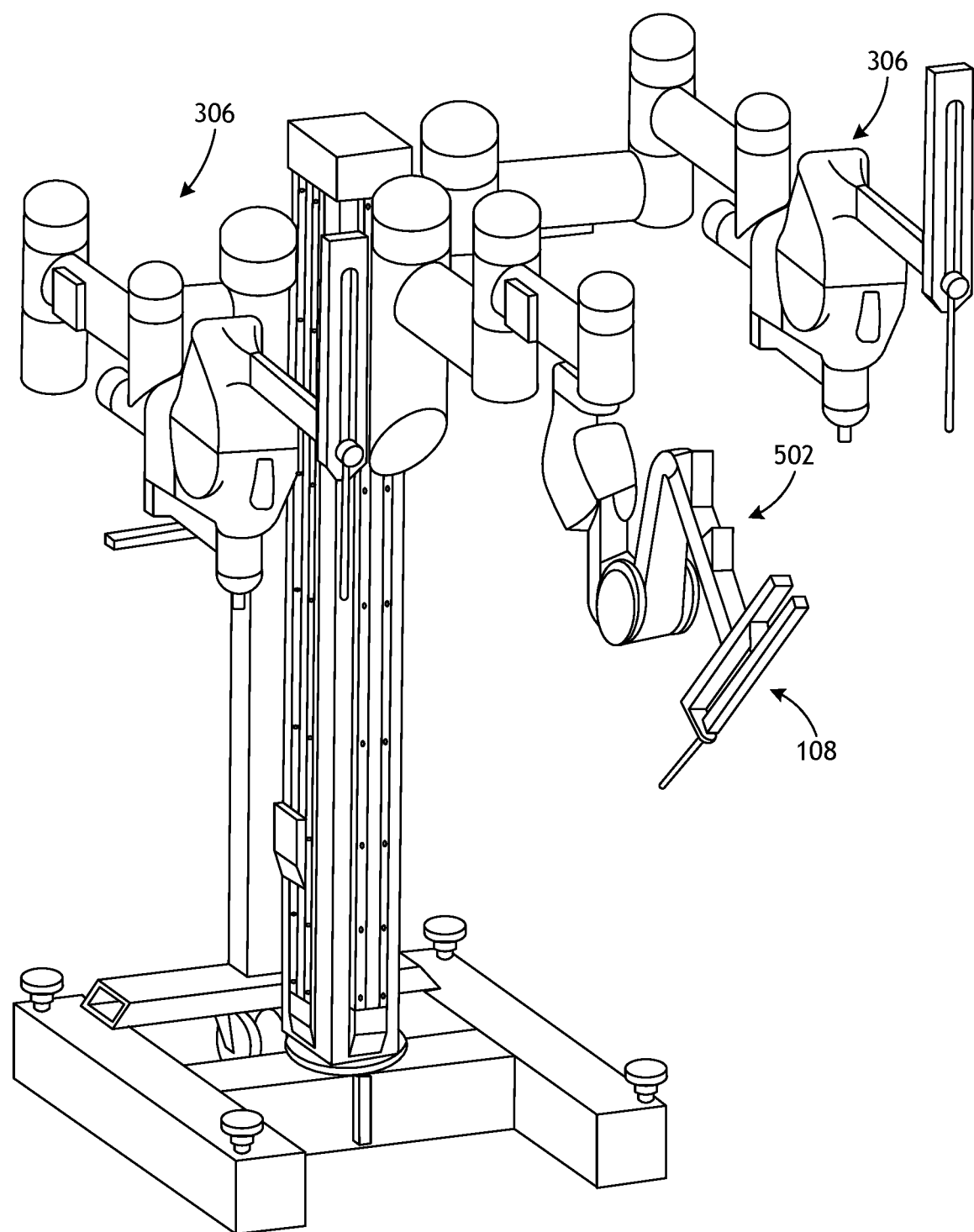
FIG. 5 is a perspective view of an alternative example robotic manipulator.

FIG. 5 is a perspective view of an alternative example robotic manipulator 502, used in conjunction with two robotic manipulators similar to the robotic manipulators 306 described in FIG. 4. As illustrated, a surgical instrument 108 is supported by the robotic manipulator 502 between the two robotic manipulators 306 generally described above. Those of ordinary skill in the art will appreciate that various embodiments of the present invention may incorporate a wide variety of alternative robotic structures, including those described in U.S. Pat. No. 5,878,193, the contents of which are hereby incorporated by reference. Additionally, while the data communication between a robotic component and the processor of the robotic surgical system is primarily described herein with reference to communication between the surgical instrument 108 and the master controller 102a (FIG. 2), it should be understood that similar communication may take place between circuitry of a robotic manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like.

Figure 6:
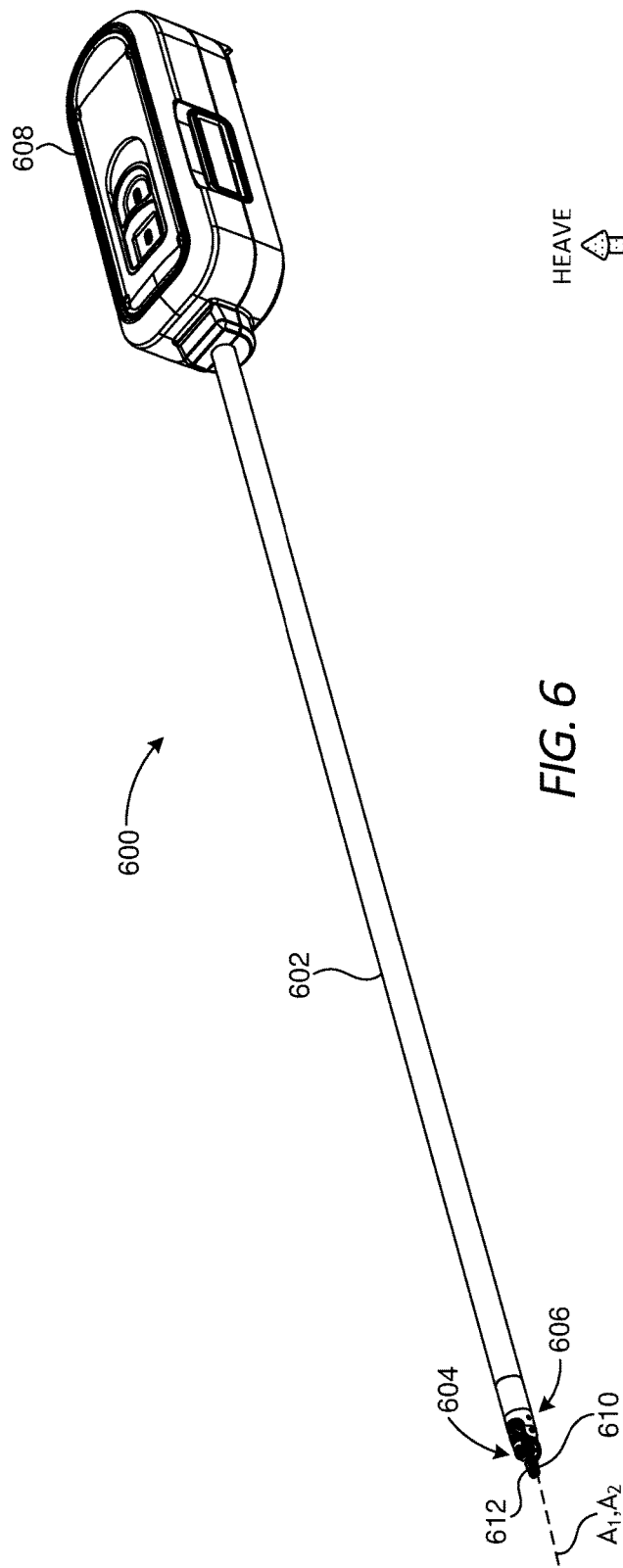
FIG. 6 is a side view of an example surgical tool that may incorporate some or all of the principles of the present disclosure.

FIG. 6 is side view of an example surgical tool 600 that may incorporate some or all of the principles of the present disclosure. The surgical tool 600 may be the same as or similar to the surgical instrument(s) 108 of FIGS. 1 and 3-5) and, therefore, may be used in conjunction with a robotic surgical system, such as the robotic surgical system 100 of FIG. 1. Accordingly, the surgical tool 600 may be designed to be releasably coupled to a tool driver included in the robotic surgical system 100.

As illustrated, the surgical tool 600 includes an elongate shaft 602, an end effector 604, a wrist 606 (alternately referred to as a "wrist joint") that couples the end effector 604 to the distal end of the shaft 602, and a drive housing 608 coupled to the proximal end of the shaft 602. In applications where the surgical tool 600 is used in conjunction with a robotic surgical system (e.g., the robotic surgical system 100 of FIG. 1), the drive housing 608 can include coupling features that releasably couple the surgical tool 600 to the robotic surgical system. It will be appreciated, however, that the principles of the present disclosure are equally applicable to surgical tools that are non-robotic and otherwise capable of manual manipulation.

The terms "proximal" and "distal" are defined herein relative to a robotic surgical system having an interface configured to mechanically and electrically couple the surgical tool 600 (e.g., the housing 608) to a robotic manipulator. The term "proximal" refers to the position of an element closer to the robotic manipulator and the term "distal" refers to the position of an element closer to the end effector 604 and thus further away from the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 600, the end effector 604 is configured to move (pivot) relative to the shaft 602 at the wrist 606 to position the end effector 604 at desired orientations and locations relative to a surgical site. The housing 608 includes (contains) various mechanisms designed to control operation of various features associated with the end effector 604 (e.g., clamping, firing, rotation, articulation, energy delivery, etc.). In at least some embodiments, the shaft 602 (and hence the end effector 604 coupled thereto) is configured to rotate about a longitudinal axis $A_1$ of the shaft 602. In such embodiments, at least one of the mechanisms included (housed) in the housing 608 is configured to control rotational movement of the shaft 602 about the longitudinal axis $A_1$.

The surgical tool 600 can have any of a variety of configurations capable of performing at least one surgical function. For example, the surgical tool 600 may include, but is not limited to, forceps, a grasper, a needle driver, scissors, an electro cautery tool, a stapler, a clip applier, a suction tool, an irrigation tool, an imaging device (e.g., an endoscope or ultrasonic probe), or any combination thereof. In some embodiments, the surgical tool 600 may be configured to apply energy to tissue, such as radiofrequency (RF) energy.

The shaft 602 is an elongate member extending distally from the housing 608 and has at least one lumen extending therethrough along its axial length. In some embodiments, the shaft 602 may be fixed to the housing 608, but could alternatively be rotatably mounted to the housing 608 to allow the shaft 602 to rotate about the longitudinal axis $A_1$. In yet other embodiments, the shaft 602 may be releasably coupled to the housing 608, which may allow a single housing 608 to be adaptable to various shafts having different end effectors.

The end effector 604 can have a variety of sizes, shapes, and configurations. In the illustrated embodiment, the end effector 604 includes opposing jaws 610, 612 configured to move (articulate) between open and closed positions. Accordingly, the end effector 604 can comprise, but is not limited to, a tissue grasper, a clip applier, scissors, a needle driver, a babcock including a pair of opposed grasping jaws, etc. One or both of the jaws 610, 612 may be configured to pivot at the wrist 606 to articulate the end effector 604 between the open and closed positions.

Figure 7:
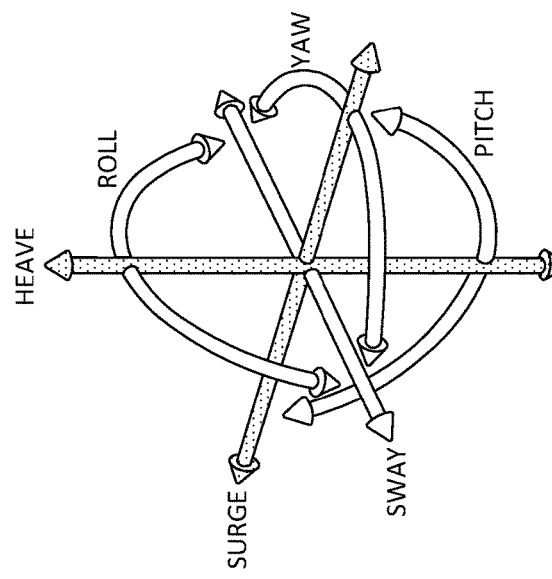
FIG. 7 illustrates potential degrees of freedom in which the wrist of FIG. 1 may be able to articulate (pivot).

FIG. 7 illustrates the potential degrees of freedom in which the wrist 606 may be able to articulate (pivot). The wrist 606 can have any of a variety of configurations. In general, the wrist 606 comprises a joint configured to allow pivoting movement of the end effector 604 relative to the shaft 602. The degrees of freedom of the wrist 606 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 604) with respect to a given reference Cartesian frame. As depicted in FIG. 7, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 606 (e.g., X-axis), yaw movement about a second axis of the wrist 606 (e.g., Y-axis), and combinations thereof to allow for 360° rotational movement of the end effector 604 about the wrist 606. In other applications, the pivoting motion can be limited to movement in a single plane, e.g., only pitch movement about the first axis of the wrist 606 or only yaw movement about the second axis of the wrist 606, such that the end effector 604 moves only in a single plane.

Referring again to FIG. 6, the surgical tool 600 includes a plurality of drive cables (obscured in FIG. 6) that form part of a cable driven motion system configured to facilitate movement (articulation) of the end effector 604 relative to the shaft 602. Moving the drive cables moves the end effector 604 between an unarticulated position and an articulated position. The end effector 604 is depicted in FIG. 6 in the unarticulated position where a longitudinal axis $A_2$ of the end effector 604 is substantially aligned with the longitudinal axis $A_1$ of the shaft 602, such that the end effector 604 is at a substantially zero angle relative to the shaft 602. Due factors such as manufacturing tolerance and precision of measurement devices, the end effector 604 may not be at a precise zero angle relative to the shaft 602 in the unarticulated position, but nevertheless be considered "substantially aligned" thereto. In the articulated position, the longitudinal axes $A_1$, $A_2$ would be angularly offset from each other such that the end effector 604 is at a non-zero angle relative to the shaft 602.

Figure 8:
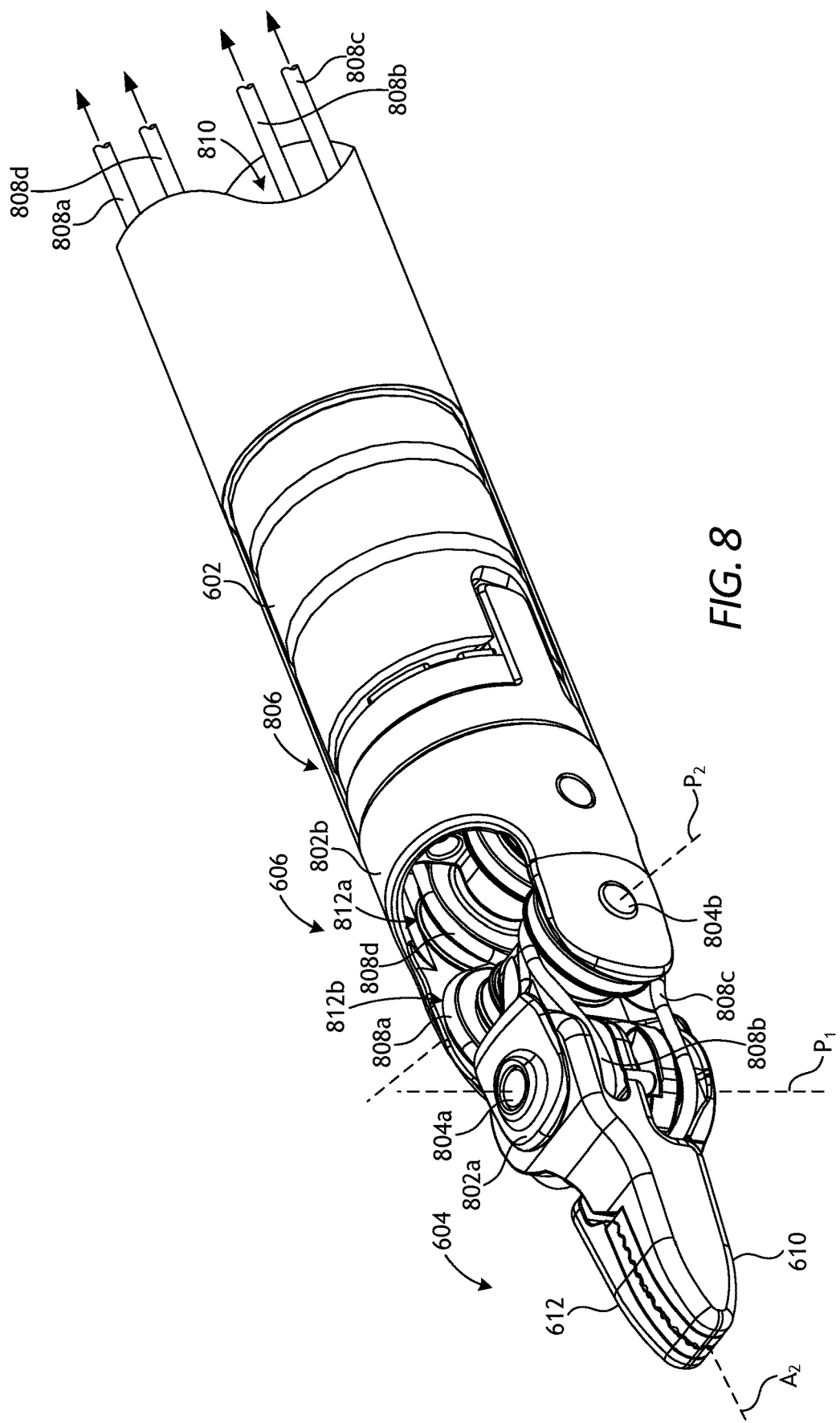
FIG. 8 is an enlarged isometric view of the distal end of the surgical tool of FIG. 1.

FIG. 8 is an enlarged isometric view of the distal end of the surgical tool 600 of FIG. 6. More specifically, FIG. 8 depicts enlarged views of the end effector 604 and the wrist 606, with the end effector 604 in the unarticulated position where the jaws 610, 612 are closed. The wrist 606 operatively couples the end effector 604 to the shaft 602. To accomplish this, the wrist 606 includes a distal clevis 802a and a proximal clevis 802b. The end effector 604 (i.e., the jaws 610, 612) is rotatably mounted to the distal clevis 802a at a first axle 804a, the distal clevis 802a is rotatably mounted to the proximal clevis 802b at a second axle 804b, and the proximal clevis 802b is coupled to a distal end 806 of the shaft 602.

The wrist 606 provides a first pivot axis $P_1$ that extends through the first axle 804a and a second pivot axis $P_2$ that extends through the second axle 804b. The first pivot axis $P_1$ is substantially perpendicular (orthogonal) to the longitudinal axis $A_2$ of the end effector 604, and the second pivot axis $P_2$ is substantially perpendicular (orthogonal) to both the longitudinal axis $A_2$ and the first pivot axis $P_1$. Movement about the first pivot axis $P_1$ provides "yaw" articulation of the end effector 604, and movement about the second pivot axis $P_2$ provides "pitch" articulation of the end effector 604. In the illustrated embodiment, the jaws 610, 612 are mounted at the first pivot axis $P_1$, thereby allowing the jaws 610, 612 to pivot relative to each other to open and close the end effector 604 or alternatively pivot in tandem to articulate the orientation of the end effector 604.

A plurality of drive cables, shown as drive cables 808a, 808b, 808c, and 808d, extend longitudinally within a lumen 810 defined by the shaft 602 and pass through the wrist 606 to be operatively coupled to the end effector 604. The drive cables 808a-d form part of the cable driven motion system briefly described above, and may be referred to and otherwise characterized as cables, bands, lines, cords, wires, ropes, strings, twisted strings, elongate members, etc. The drive cables 808a-d can be made from a variety of materials including, but not limited to, metal (e.g., tungsten, stainless steel, etc.) or a polymer. Example drive cables are described in U.S. Patent Pub. No. 2015/0209965 entitled "Compact Robotic Wrist," and U.S. Patent Pub. No. 2015/0025549 entitled "Hyperdexterous Surgical System," the contents of which are hereby incorporated by reference. The lumen 810 can be a single lumen, as illustrated, or can alternatively comprise a plurality of independent lumens that each receive one or more of the drive cables 808a-d.

The drive cables 808a-d extend proximally from the end effector 604 to the drive housing 608 (FIG. 6) where they are operatively coupled to various actuation mechanisms or devices housed (contained) therein to facilitate longitudinal movement (translation) of the drive cables 808a-d within the lumen 810. Selective actuation of all or a portion of the drive cables 808a-d causes the end effector 604 (e.g., one or both of the jaws 610, 612) to articulate (pivot) relative to the shaft 602. More specifically, selective actuation causes a corresponding drive cable 808a-d to translate longitudinally within the lumen 810 and thereby cause pivoting movement of the end effector 604. One or more drive cables 808a-d, for example, may translate longitudinally to cause the end effector 604 to articulate (e.g., both of the jaws 610, 612 angled in a same direction), to cause the end effector 604 to open (e.g., one or both of the jaws 610, 612 move away from the other), or to cause the end effector 604 to close (e.g., one or both of the jaws 610, 612 move toward the other).

Moving the drive cables 808a-d can be accomplished in a variety of ways, such as by triggering an associated actuator or mechanism operatively coupled to or housed within the drive housing 608 (FIG. 6). Moving a given drive cable 808a-d constitutes applying tension (i.e., pull force) to the given drive cable 808a-d in a proximal direction, which causes the given drive cable 808a-d to translate and thereby cause the end effector 604 to move (articulate) relative to the shaft 602.

The wrist 606 includes a first plurality of pulleys 812a and a second plurality of pulleys 812b, each configured to interact with and redirect the drive cables 808a-d for engagement with the end effector 604. The first plurality of pulleys 812a is mounted to the proximal clevis 802b at the second axle 804b and the second plurality of pulleys 812b is also mounted to the proximal clevis 802b but at a third axle 804c located proximal to the second axle 804b. The first and second pluralities of pulleys 812a,b cooperatively redirect the drive cables 808a-d through an "S" shaped pathway before the drive cables 808a-d are operatively coupled to the end effector 604.

In at least one embodiment, one pair of drive cables 808a-d is operatively coupled to each jaw 610, 612 and configured to "antagonistically" operate the corresponding jaw 610, 612. In the illustrated embodiment, for example, the first and second drive cables 808a,b may be coupled at the first jaw 610, and the third and fourth drive cables 808c,d may be coupled at the second jaw 612. Actuation of the first drive cable 808a acts on and pivots the first jaw 610 about the first pivot axis $P_1$ toward the open position. In contrast, actuation of the second drive cable 808b also acts on and pivots the first jaw 610 about the first pivot axis $P_1$ in the opposite direction and toward the closed position. Similarly, actuation of the third drive cable 808c acts and pivots the second jaws 612 about the first pivot axis $P_1$ toward the open position, while actuation of the fourth drive cable 808d also acts on but pivots the second jaws 612 about the first pivot axis $P_1$ in the opposite direction and toward the closed position.

Accordingly, the drive cables 808a-d may be characterized or otherwise referred to as "antagonistic" cables that cooperatively (yet antagonistically) operate to cause relative or tandem movement of the first and second jaws 610, 612. When the first drive cable 808a is actuated (moved), the second drive cable 808b naturally follows as coupled to the first drive cable 808a, and vice versa. Similarly, when the third drive cable 808c is actuated, the fourth drive cable 808d naturally follows as coupled to the third drive cable 808c, and vice versa.

Moreover, coordinated actuation of the drive cables 808a-d may also articulate the end effector 604 about the second pivot axis $P_2$. Consequently, the end effector 604 can articulate with multiple degrees of freedom, e.g., a degree of freedom by articulating about the first pivot axis $P_1$ and another degree of freedom by articulating about the second pivot axis $P_2$. The wrist 606 in this embodiment is pivotable about the second pivot axis $P_2$ in a single plane, e.g., in one of pitch and yaw, and the end effector 604 is pivotable about the first pivot axis $P_1$ in a single, different plane, e.g., the other of pitch and yaw.

Figure 9:
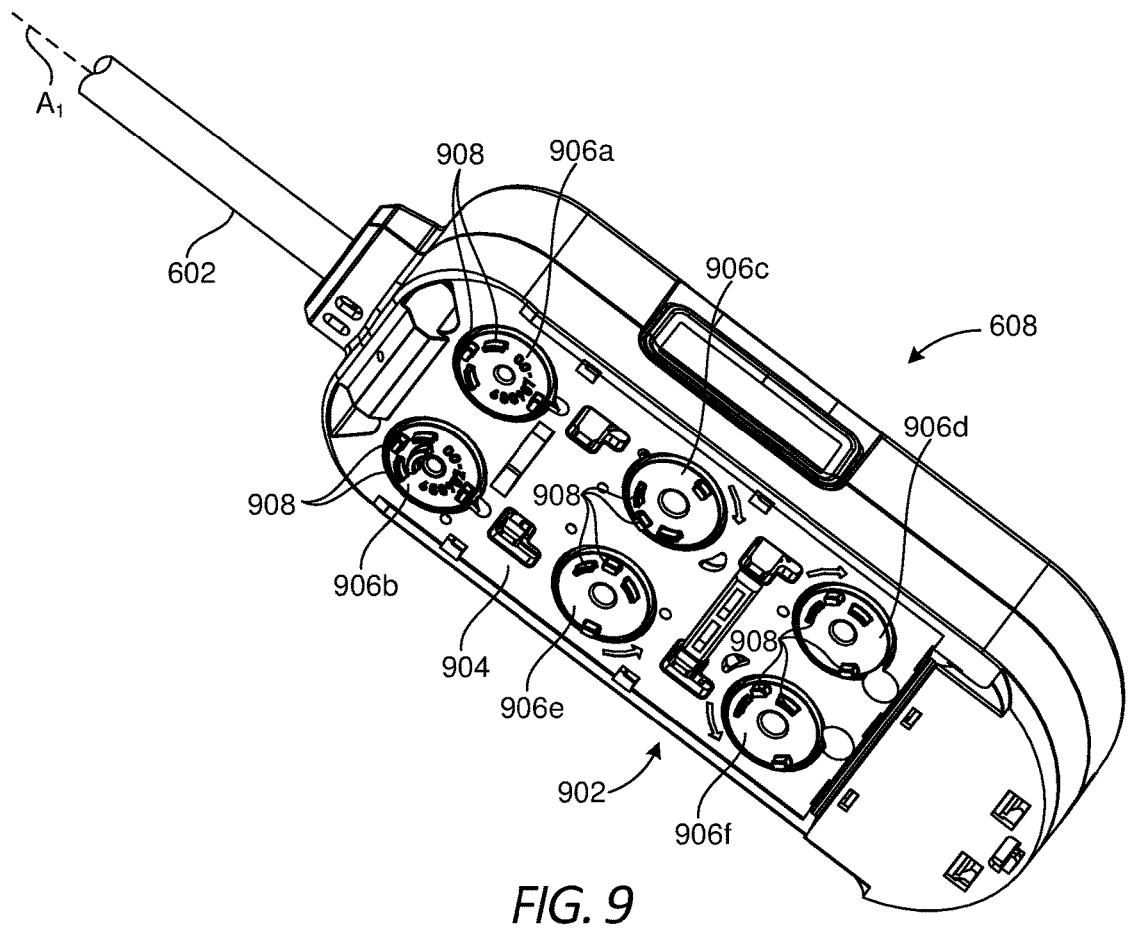
FIG. 9 is a bottom view of the drive housing of the surgical tool of FIG. 6.

FIG. 9 is a bottom view of the drive housing 608, according to one or more embodiments. As illustrated, the drive housing 608 (alternately referred to as a "puck") may include a tool mounting portion 902 used to operatively couple the drive housing 608 to a tool driver of a robotic manipulator (e.g., the robotic manipulators 306, 502 of FIGS. 3 and 5, respectively). The tool mounting portion 902 may releasably couple the drive housing 608 to a tool driver in a variety of ways, such as by clamping thereto, clipping thereto, or slidably mating therewith. In some embodiments, the tool mounting portion 902 may include an array of electrical connecting pins, which may be coupled to an electrical connection on the mounting surface of the tool driver. While the tool mounting portion 902 is described herein with reference to mechanical, electrical, and magnetic coupling elements, it should be understood that a wide variety of telemetry modalities might be used, including infrared, inductive coupling, or the like.

The tool mounting portion 902 includes and otherwise provides an interface 904 configured to mechanically, magnetically, and/or electrically couple the drive housing 608 to the tool driver. As illustrated, the interface 904 includes and supports a plurality of inputs, shown as drive inputs 906a, 906b, 906c, 906d, 906e, and 906f. In at least one embodiment, each drive input 906a-f comprises a rotatable disc configured to align with and couple to a corresponding actuator of a given tool driver. Moreover, each drive input 906a-f provides or defines one or more surface features 908 configured to align with mating surface features provided on the corresponding actuator. The surface features 908 can include, for example, various protrusions and/or indentations that facilitate a mating engagement. In some embodiments, some or all of the drive inputs 906a-f may include one surface feature 908 that is positioned closer to an axis of rotation of the associated drive input 906a-f than the other surface feature(s) 908. This may help to ensure positive angular alignment of each drive input 906a-f.

In some embodiments, actuation of the first drive input 906a may be configured to control rotation of the elongate shaft 602 about its longitudinal axis $A_1$. The elongate shaft 602 may be rotated clockwise or counter-clockwise depending on the rotational actuation of the first drive input 906a. In some embodiments, actuation of the second drive input 906b may be configured to control a lockout mechanism (alternately referred to as a deadbolt), which locks the end effector 604 (FIGS. 6 and 8) in a predetermined pose or position. In some embodiments, actuation of the third, fourth, fifth, and sixth drive inputs 906c-f may be configured to operate movement (axial translation) of the drive cables 808a-d (FIG. 8), respectively, which results in the articulation of the end effector 604. Each of the drive inputs 906a-f may be actuated based on user inputs communicated to a tool driver coupled to the interface 904, and the user inputs may be received via a computer system incorporated into the robotic surgical system.

Figure 10:
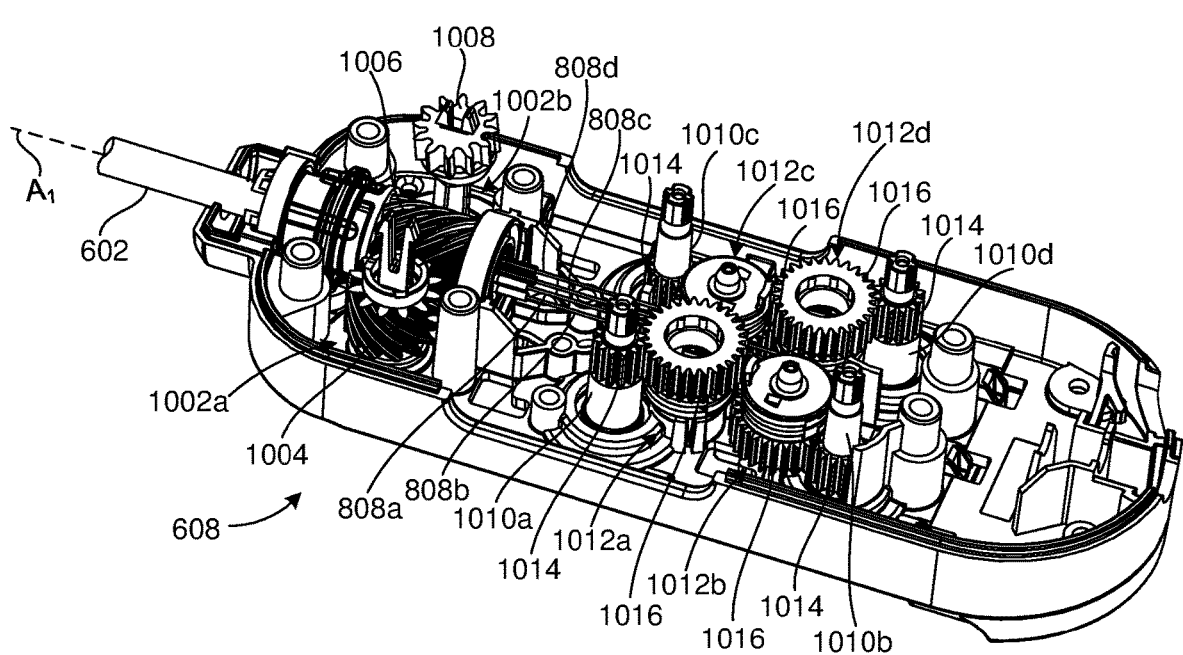
FIG. 10 is an isometric exposed view of the interior of the drive housing of the surgical tool of FIG. 6.

FIG. 10 is an isometric exposed view of the interior of the drive housing 608, according to one or more embodiments. Several component parts that may be otherwise contained within the drive housing 608 are not shown in FIG. 10 to enable discussion of the depicted component parts. As illustrated, a first capstan 1002a and a second capstan 1002b are contained (housed) within the drive housing 608. The first capstan 1002a may be operatively coupled to or extend from the first drive input 906a (FIG. 9), and the second capstan 1002b may be operatively coupled to or extend from the second drive input 906b (FIG. 9). Accordingly, actuation of the first drive input 906a results in rotation of the first capstan 1002a and actuation of the second drive input 906b results in rotation of the second capstan 1002b.

A spiral worm drive gear 1004 is coupled to or forms part of the first capstan 1002a. The spiral worm drive gear 1004 may be configured to mesh and interact with a driven gear 1006 secured within the drive housing 608 and operatively coupled to the shaft 602 such that rotation of the driven gear 1006 correspondingly rotates the shaft 602. Accordingly, rotation of the spiral worm drive gear 1004 (via actuation of the first drive input 906a of FIG. 9) will drive the driven gear 1006 and thereby control rotation of the elongate shaft 602 about the longitudinal axis $A_1$.

In some embodiments, the second capstan 1002b may have a pinion gear 1008 coupled thereto and configured to mesh and interact with a rack (not shown) contained within the drive housing 608. The rack may be operatively coupled to a lockout mechanism that is movable to lock the end effector 604 (FIGS. 6 and 8) in a predetermined pose or position. Accordingly, rotation of the pinion gear 1008 (via actuation of the second drive input 906b of FIG. 9) will control the lockout mechanism and thereby lock and unlock the end effector 604 when desired.

The drive housing 608 further contains or houses a first input shaft 1010a, a second input shaft 1010b, a third input shaft 1010c, and a fourth input shaft 1010d. In the illustrated embodiment, the first input shaft 1010a is operatively coupled to or extends from the third drive input 906c (FIG. 9), the second input shaft 1010b is operatively coupled to or extends from the fourth drive input 906d (FIG. 9), the third input shaft 1010c is operatively coupled to or extends from the fifth drive input 906e (FIG. 9), and the fourth input shaft 1010d is operatively coupled to or extends from the sixth drive input 906f (FIG. 9). Accordingly, actuation of the third drive input 906c results in rotation of the first input shaft 1010a, actuation of the fourth drive input 906d results in rotation of the second input shaft 1010b, actuation of the fifth drive input 906e results in rotation of the third input shaft 1010c, and actuation of the sixth drive input 906f results in rotation of the fourth input shaft 1010d. While four input shafts 1010a-d are depicted in FIG. 10, it is contemplated herein to include more or less than four, without departing from the scope of the disclosure.

The drive housing 608 further contains or houses a first drive cable capstan 1012a, a second drive cable capstan 1012b, a third drive cable capstan 1012c, and a fourth drive cable capstan 1012d. Each drive cable capstan 1012a-d is rotatably mounted within the drive housing 608 and one of the drive cables 808a-d is operatively coupled to a corresponding one of the drive cable capstans 1012a-d. More specifically, the first drive cable 808a is coupled to the first drive cable capstan 1012a, the second drive cable 808b is coupled to the second drive cable capstan 1012b, the third drive cable 808c is coupled to the third drive cable capstan 1012c, and the fourth drive cable 808d is coupled to the fourth drive cable capstan 1012d.

As illustrated, each input shaft 1010a-d has a drive gear 1014 coupled thereto or forming part thereof, and each drive cable capstan 1012a-d has a driven gear 1016 coupled thereto or forming part thereof. Each drive gear 1014 is positioned to mesh and interact with a corresponding driven gear 1016. In some embodiments, the drive and driven gears 1014, 1016 may comprise mating spur gears. Accordingly, rotation of the first input shaft 1010a (via actuation of the third drive input 906c of FIG. 9) will correspondingly rotate the associated drive gear 1014 and drive the associated driven gear 1016 to control movement of the first drive cable 808a; rotation of the second input shaft 1010b (via actuation of the fourth drive input 906d of FIG. 9) will correspondingly rotate the associated drive gear 1014 and drive the associated driven gear 1016 to control movement of the second drive cable 808b; rotation of the third input shaft 1010c (via actuation of the fifth drive input 906e of FIG. 9) will correspondingly rotate the associated drive gear 1014 and drive the associated driven gear 1016 to control movement of the third drive cable 808c; and rotation of the fourth input shaft 1010d (via actuation of the sixth drive input 906f of FIG. 9) will correspondingly rotate the associated drive gear 1014 and drive the associated driven gear 1016 to control movement of the fourth drive cable 808d.

Figure 11:
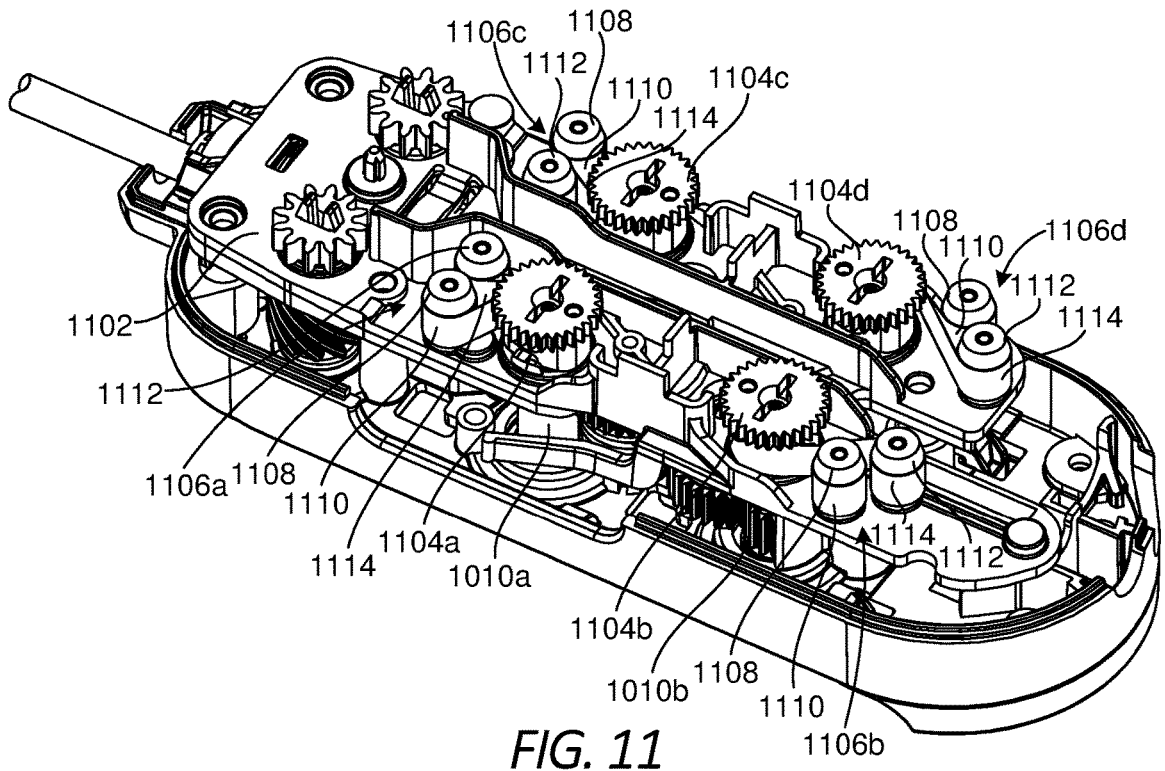
FIG. 11 is another isometric exposed view of the interior of the drive housing of the surgical tool of FIG. 6.

FIG. 11 is another isometric exposed view of the interior of the drive housing 608 that shows additional internal component parts, according to one or more embodiments. The drive housing 608 may include a chassis 1102 configured to be mounted within the drive housing 608 to support various internal component parts.

As illustrated, the drive housing 608 may further contain (house) a first shaft extension 1104a, a second shaft extension 1104b, a third shaft extension 1104c, and a fourth shaft extension 1104d. The first shaft extension 1104a extends from the first input shaft 1010a, the second shaft extension 1104b extends from the second input shaft 1010b, the third shaft extension 1104c extends from the third input shaft 1010c (obscured in FIG. 11, see FIG. 10), and the fourth shaft extension 1104d extends from the fourth input shaft 1010d (obscured in FIG. 11, see FIG. 10). In some embodiments, each shaft extension 1104a-d may be removably coupled to its corresponding input shaft 1010a-d. In other embodiments, each shaft extension 1104a-d may form an integral extension (part) of its corresponding input shaft 1010a-d. In either scenario, movement (rotation) of a given input shaft 1010a-d correspondingly moves (rotates) the associated shaft extension 1104a-d in the same angular direction. For purposes of the present disclosure, the shaft extensions 1104a-d are considered part of the corresponding input shaft 1010a-d in the sense that any mechanical loads applied to the shaft extensions 1104a-d will be equally applied to the corresponding input shaft 1010a-d, and vice versa.

The drive housing 608 may further contain (house) a first spring assembly 1106a, a second spring assembly 1106b, a third spring assembly 1106c, and a fourth spring assembly 1106a. The first spring assembly 1106a may be operatively coupled to the first input shaft 1010a, the second spring assembly 1106b may be operatively coupled to the second input shaft 1010b, the third spring assembly 1106c may be operatively coupled to the third input shaft 1010c, and the fourth spring assembly 1106d may be operatively coupled to the fourth input shaft 1010d. While FIG. 11 depicts four spring assemblies 1106a-d, each operatively coupled to a corresponding input shaft 1010a-d, it is contemplated herein to have more or less than four spring assemblies 1106a-d, without departing from the scope of the disclosure.

As used herein, the term "operatively coupled" can refer to a direct or indirect coupling engagement between two structural component parts. In the illustrated embodiment, for example, each spring assembly 1106a-d is directly coupled to a corresponding one of the shaft extensions 1104a-d, which indirectly couples the spring assemblies 1106a-d to the associated input shafts 1010a-d. In other embodiments, however, each spring assembly 1106a-d may alternatively be directly coupled to the associated input shafts 1010a-d in keeping with the definition of "operatively coupled."

As illustrated, each spring assembly 1106a-d includes at least one winder drum 1108 and a constant force spring 1110 that extends between the winder drum 1108 and an adjacent input shaft 1010a-d (i.e., an adjacent shaft extension 1104a-d). Each winder drum 1108 comprises a free-spinning hub rotatably mounted to the chassis 1102. One end of the corresponding constant force spring 1110 is wrapped about the winder drum 1108 one or more times in a first angular direction. The other end of the constant force spring 1110 is wrapped about the adjacent input shaft 1010a-d (i.e., the adjacent shaft extension 1104a-d) one or more times, but in a second angular direction opposite the first angular direction.

Each constant force spring 1110 comprises a spring that exerts a known constant force and/or resistance over its range of motion. In some embodiments, for example, the constant force spring 1110 may comprise a rolled ribbon of spring steel that is relaxed when it is fully rolled up. In other embodiments, one or more of the constant force springs 1110 may comprise a ribbon or strip of material made of aluminum, titanium, a polymer, an elastomer, a fiber mesh, or any combination of the foregoing. As it unrolls from the winder drum 1108 in one direction or from the corresponding input shaft 1010a-d (i.e., the adjacent shaft extension 1104a-d) in the opposite direction, the constant force spring 1110 provides a constant resistance. Because the geometry of the constant force spring 1110 remains nearly constant as the constant force spring 1110 unrolls, the resulting resistance force is nearly or entirely constant. This is in contrast to typical torsion springs, which tend to increase in resistance over their range of motion.

In operation, each spring assembly 1106a-d helps maintain a minimum level of force (resistance) on a corresponding drive cable 808a-d (FIGS. 8 and 10), which helps prevent the corresponding drive cable 808a-d from relaxing (e.g., slackening). More specifically, since each constant force spring 1110 is operatively coupled to a corresponding input shaft 1010a-d, which drives a corresponding drive cable capstan 1010a-d and thereby moves a corresponding drive cable 808a-d, any torque resistance exhibited by the constant force spring 1110 will be transmitted to and otherwise assumed by the corresponding drive cable 808a-d. As each input shaft 1010a-d is actuated to rotate a corresponding drive cable capstan 1010a-d and thereby move a corresponding drive cable 808a-d, the associated constant force spring 1110 either unrolls from or retracts back onto the associated winder drum 1108 and simultaneously provides a known and constant torque resistance across its entire range of motion. As a result, a constant torque is assumed by the corresponding drive cable 808a-d, which keeps the corresponding drive cable 808a-d taut at all times during operation.

The constant resistance force provided by the constant force springs 1110 may be especially advantageous for robotic surgical instruments, such as the surgical tool 600 of FIG. 6. Because the constant force spring 1110 provides a constant torque over its displacement, the force required from a robotic tool driver (e.g., the robotic manipulator 306 of FIG. 3) need not be altered to adjust for changing torque resistance. In contrast, other surgical tools use torsion springs to counteract drive cable movement. Such torsion springs exhibit a torque rating that varies widely with angular displacement, and otherwise provides increasing resistance across its range of motion. This requires a robotic tool driver to alter the force required to move the drive cables during operation to account for continual changes in the torque resistance.

Moreover, the torsion springs in other surgical tools are often directly coupled to the drive cable capstans to resist movement of the drive cables. In contrast, the presently disclosed constant force springs 1110 are operatively coupled to the corresponding input shafts 1010*a-d*, not the drive cable capstans 1012*a-d*. This ensures that the intermeshed teeth of the drive gear 1014 and corresponding driven gear 1016 are always loaded. This may prove advantageous in removing clearances and slot length between the teeth, which can result in quicker responses as compared to prior art gearing.

In some embodiments, the constant resistance provided by the spring assemblies 1106*a-d* may be altered and otherwise optimized based on a thickness of the associated constant force spring 1110. The thicker the material (e.g., a metal) of the constant force spring 1110, the more torque resistance the constant force spring 1110 is able to provide.

In other embodiments, however, the resistance provided by the spring assemblies 1106*a-d* may be altered or optimized by including one or more additional constant force springs. More specifically, in some embodiments, one or more of the spring assemblies 1106*a-d* may include a second winder drum 1112 and a second constant force spring 1114 that extends between the second winder drum 1112 and the adjacent input shaft 1010*a-d* (i.e., the adjacent shaft extension 1104*a-d*). Each second winder drum 1112 may be substantially similar to the first winder drum 1108, and each second constant force spring 1114 may be substantially similar to the first constant force spring 1110. More specifically, each second winder drum 1112 comprises a free-spinning hub rotatably mounted to the chassis 1102, and the corresponding second constant force spring 1114 is wrapped about the second winder drum 1112 one or more times in a first angular direction. The second constant force spring 1114 is also wrapped about the adjacent input shaft 1010*a-d* (i.e., the adjacent shaft extension 1104*a-d*) one or more times, but in a second angular direction opposite the first angular direction.

Adding the second constant force spring 1114 and the associated second winder drum 1112 to the spring assemblies 1106*a-d* allows the constant torque resistance provided by each spring assembly 1106*a-d* to be broken up into two load-bearing modules. Moreover, this may prove advantageous from a packaging perspective. While the constant torque resistance may be adjusted by altering the size and thickness of the constant force spring 1114, this can cause manufacturing issues. It may instead be easier to simply add the second constant force spring 1114 and the associated second winder drum 1112 to avoid such manufacturing issues.

Figure 12:
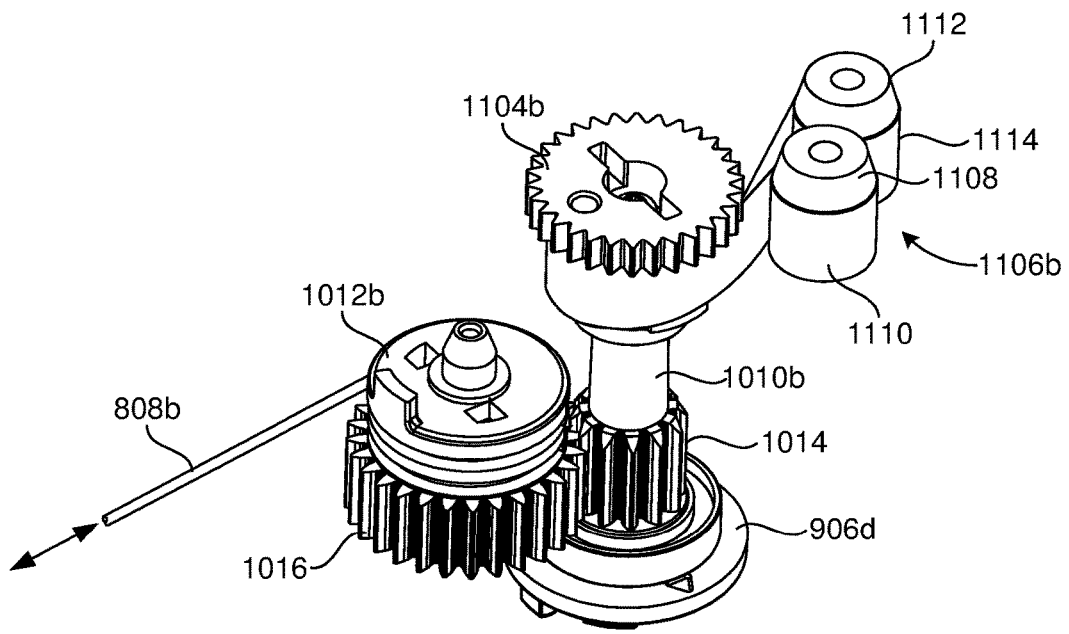
FIG. 12 is an isometric view of the second input shaft, the second drive cable capstan, and the second spring assembly cooperatively arranged for operation.

FIG. 12 is an isometric view of the second input shaft 1010*b*, the second drive cable capstan 1012*b*, and the second spring assembly 1106*b* cooperatively arranged for operation, according to one or more embodiments. While discussing specifics and details of the second input shaft 1010*b*, the second drive cable capstan 1012*b*, and the second spring assembly 1106*b*, the following description is equally applicable to any of the input shafts 1010*a-d*, drive cable capstans 1012*a-d*, and spring assemblies 1106*a-d* described herein with reference to FIGS. 10 and 11. Accordingly, the following discussion is equally applicable to operation of the first, third, and fourth input shafts 1010*a,c,d*, drive cable capstans 1012*a,c,d*, and spring assemblies 1106*a,c,d*, respectively.

As mentioned above, the second input shaft 1010*b* is operatively coupled to or extends from the fourth drive input 906*d*. As a result, actuation of the fourth drive input 906*d* correspondingly rotates the second input shaft 1010*b*, its associated drive gear 1014, and the second shaft extension 1104*b*. Moreover, as also mentioned above, the second drive cable 808*b* is coupled to the second drive cable capstan 1012*b*, which includes a driven gear 1016 configured to mesh and interact with the drive gear 1014 of the second input shaft 1010*b*. Consequently, actuating the fourth drive input 906*d* rotates the second input shaft 1010*b*, which correspondingly rotates the second drive cable capstan 1012*b* to control longitudinal movement of the second drive cable 808*b* in either longitudinal direction.

As the second input shaft 1010*b* rotates, the second spring assembly 1106*b* helps maintain constant torque resistance on the second drive cable 808*b*, which helps prevent the second drive cable 808*b* from relaxing (e.g., slackening). More specifically, the constant force spring 1110 either unrolls from or retracts back onto the winder drum 1108 as the second input shaft 1010*b* rotates the second drive cable capstan 1010*b*. Across its entire range of motion in either angular direction of rotation, the constant force spring 1110 provides a known and constant torque resistance to the second input shaft 1010*b*. This constant torque resistance is transmitted to the second drive cable capstan 1012*b* and assumed by the second drive cable 808*b* to keep the second drive cable 808*b* taut at all times during operation.

The constant torque resistance provided by the second spring assembly 1106*b* may be increased or otherwise optimized by including the second constant force spring 1114 and its associated second winder hub 1112. In the illustrated embodiment, the second constant force spring 1114 combines with or supplements the first constant force spring 1110 by extending jointly between the second winder drum 1112 and the second input shaft 1010*b* (i.e., the second shaft extension 1104*b*). As the second input shaft 1010*b* rotates in either angular direction, the constant force springs 1110, 1114 provide a known and constant torque resistance to the second input shaft 1010*b* across their entire range of motion. This constant torque resistance is transmitted to the second drive cable capstan 1012*b* and assumed by the second drive cable 808*b* to keep the second drive cable 808*b* taut at all times during operation.

Accordingly, the second spring assembly 1106*b* may prove advantageous in maintaining a minimum level of force on the second drive cable 808*b*, and prevent the second drive cable 808*b* from ever slackening. The second spring assembly 1106*b* provides a simple spool-to-spool take up that results in a constant torque resistance being applied to the second drive cable 808*b*. In contrast to conventional torsion springs that increase resistance with displacement, as the second drive cable capstan 1012*b* is rotated, the torque resistance stays constant. Moreover, with conventional torsion springs, the wrist 606 (FIGS. 6 and 8) will tend to naturally return (or substantially return) to a known origination position after being articulated to a particular position under the spring force of the torsion springs. In contrast, with the constant force springs 1110, 1114 of the second spring assembly 1106*b*, one can articulate the wrist 606 to a particular position and the wrist 606 will have more of a tendency to stay in that particular position. This is because the constant force springs 1110, 1114 will reach equilibrium between themselves during operation.

Embodiments disclosed herein include:

A. A surgical tool that includes a drive housing having an input shaft and a drive cable capstan arranged within the drive housing, the input shaft including a drive gear and the drive cable capstan including a driven gear intermeshed with the drive gear such that rotation of the input shaft rotates the drive cable capstan, an elongate shaft that extends from the drive housing, an end effector operatively coupled to a distal end of the elongate shaft, a drive cable coupled to the drive cable capstan and extending to the end effector, and a spring assembly including a winder drum and a constant force spring extending between the winder drum and the input shaft, wherein the constant force spring provides a constant torque force that resists rotation of the input shaft and thereby prevents the drive cable from slackening.

B. A method of operating a surgical tool that includes positioning the surgical tool adjacent a patient for operation, the surgical tool including a drive housing having an input shaft and a drive cable capstan arranged within the drive housing, the input shaft including a drive gear and the drive cable capstan including a driven gear intermeshed with the drive gear such that rotation of the input shaft rotates the drive cable capstan, an elongate shaft that extends from the drive housing, an end effector operatively coupled to a distal end of the elongate shaft, a drive cable coupled to the drive cable capstan and extending to the end effector, and a spring assembly including a winder drum and a constant force spring extending between the winder drum and the input shaft. The method also includes actuating a drive input coupled to the input shaft and thereby rotating the input shaft and the drive cable capstan, providing a constant torque force from the constant force spring as the input shaft rotates, and resisting rotation of the input shaft with the constant torque force and thereby preventing the drive cable from slackening.

Each of embodiments A and B may have one or more of the following additional elements in any combination: Element 1: wherein a first end of the constant force spring is wrapped about the winder drum one or more times in a first angular direction, and a second end of the constant force spring is wrapped about the input shaft one or more times in a second angular direction opposite the first angular direction. Element 2: wherein the second end is coupled to a shaft extension that extends from the input shaft. Element 3: wherein the constant torque force remains constant across an entire range of motion of the constant force spring. Element 4: further comprising a chassis arranged within the drive housing, wherein the winder drum is rotatably mounted to the chassis. Element 5: wherein the constant force spring comprises a rolled ribbon of spring steel. Element 6: wherein the winder drum is a first winder drum and the constant force spring is a first constant force spring, and wherein the spring assembly further includes a second winder drum and a second constant force spring extending between the second winder drum and the input shaft, and wherein the second constant force spring provides a second constant torque force that resists rotation of the input shaft and thereby prevents the drive cable from slackening. Element 7: wherein the constant torque force is transmitted from the constant force spring to the drive cable via the input shaft and the drive cable capstan. Element 8: wherein the spring assembly is first spring assembly and the surgical tool further comprises a second spring assembly operatively coupled to a second input shaft to provide a second constant torque force that resists rotation of the second input shaft and thereby prevents a second drive cable from slackening. Element 9: wherein the constant force spring resists rotation of the input shaft in either angular direction with the constant torque force.

Element 10: wherein providing the constant torque force comprises providing a constant resistance across an entire range of motion of the constant force spring. Element 11: further comprising a chassis arranged within the drive housing, wherein the winder drum is rotatably mounted to the chassis. Element 12: wherein the winder drum is a first winder drum and the constant force spring is a first constant force spring, and wherein the spring assembly further includes a second winder drum and a second constant force spring extending between the second winder drum and the input shaft, the method further comprising providing a second constant torque force from the second constant force spring as the input shaft rotates, and resisting rotation of the input shaft with the second constant torque force and thereby preventing the drive cable from slackening. Element 13: further comprising transmitting the constant torque force from the constant force spring to the drive cable via the input shaft and the drive cable capstan. Element 14: wherein the spring assembly is first spring assembly and the surgical tool further comprises a second spring assembly operatively coupled to a second input shaft, the method further comprising providing a second constant torque force with the second spring assembly, and resisting rotation of the second input shaft with the second constant torque force and thereby preventing a second drive cable from slackening. Element 15: wherein resisting rotation of the input shaft with the constant torque force comprises resisting rotation of the input shaft in either angular direction with the constant torque force. Element 16: further comprising adjusting the constant torque force by adjusting a thickness of the constant force spring. Element 17: wherein a first end of the constant force spring is wrapped about the winder drum one or more times in a first angular direction, and a second end of the constant force spring is wrapped about the input shaft one or more times in a second angular direction opposite the first angular direction. Element 18: wherein the second end is coupled to a shaft extension that extends from the input shaft.

By way of non-limiting example, exemplary combinations applicable to A and B include: Element 1 with Element 2; and Element 17 with Element 18.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A surgical tool, comprising:
   a drive housing having an input shaft and a drive cable capstan arranged within the drive housing, the input shaft including a drive gear and the drive cable capstan including a driven gear intermeshed with the drive gear such that rotation of the input shaft rotates the drive cable capstan;
   an elongate shaft that extends from the drive housing;
   an end effector operatively coupled to a distal end of the elongate shaft;
   a drive cable coupled to the drive cable capstan and extending to the end effector; and
   a spring assembly including a winder drum and a constant force spring extending between the winder drum and the input shaft, wherein the constant force spring provides a constant torque force that resists rotation of the input shaft and thereby prevents the drive cable from slackening.

2. The surgical tool of claim 1, wherein a first end of the constant force spring is wrapped about the winder drum one or more times in a first angular direction, and a second end of the constant force spring is wrapped about the input shaft one or more times in a second angular direction opposite the first angular direction.

3. The surgical tool of claim 2, wherein the second end is coupled to a shaft extension that extends from the input shaft.

4. The surgical tool of claim 1, wherein the constant torque force remains constant across an entire range of motion of the constant force spring.

5. The surgical tool of claim 1, further comprising a chassis arranged within the drive housing, wherein the winder drum is rotatably mounted to the chassis.

6. The surgical tool of claim 1, wherein the constant force spring comprises a rolled ribbon of spring steel.

7. The surgical tool of claim 1, wherein the winder drum is a first winder drum and the constant force spring is a first constant force spring, and wherein the spring assembly further includes a second winder drum and a second constant force spring extending between the second winder drum and the input shaft, and wherein the second constant force spring provides a second constant torque force that resists rotation of the input shaft and thereby prevents the drive cable from slackening.

8. The surgical tool of claim 1, wherein the constant torque force is transmitted from the constant force spring to the drive cable via the input shaft and the drive cable capstan.

9. The surgical tool of claim 1, wherein the spring assembly is first spring assembly and the surgical tool further comprises a second spring assembly operatively coupled to a second input shaft to provide a second constant torque force that resists rotation of the second input shaft and thereby prevents a second drive cable from slackening.

10. The surgical tool of claim 1, wherein the constant force spring resists rotation of the input shaft in either angular direction with the constant torque force.

11. A method of operating a surgical tool, comprising:
    positioning the surgical tool adjacent a patient for operation, the surgical tool including:
       a drive housing having an input shaft and a drive cable capstan arranged within the drive housing, the input shaft including a drive gear and the drive cable capstan including a driven gear intermeshed with the drive gear such that rotation of the input shaft rotates the drive cable capstan;
       an elongate shaft that extends from the drive housing;
       an end effector operatively coupled to a distal end of the elongate shaft;
       a drive cable coupled to the drive cable capstan and extending to the end effector; and
       a spring assembly including a winder drum and a constant force spring extending between the winder drum and the input shaft;
    actuating a drive input coupled to the input shaft and thereby rotating the input shaft and the drive cable capstan;
    providing a constant torque force from the constant force spring as the input shaft rotates; and
    resisting rotation of the input shaft with the constant torque force and thereby preventing the drive cable from slackening.

12. The method of claim 11, wherein providing the constant torque force comprises providing a constant resistance across an entire range of motion of the constant force spring.

13. The method of claim 11, further comprising a chassis arranged within the drive housing, wherein the winder drum is rotatably mounted to the chassis.

14. The method of claim 11, wherein the winder drum is a first winder drum and the constant force spring is a first constant force spring, and wherein the spring assembly further includes a second winder drum and a second constant force spring extending between the second winder drum and the input shaft, the method further comprising:
    providing a second constant torque force from the second constant force spring as the input shaft rotates; and
    resisting rotation of the input shaft with the second constant torque force and thereby preventing the drive cable from slackening.

15. The method of claim 11, further comprising transmitting the constant torque force from the constant force spring to the drive cable via the input shaft and the drive cable capstan.

16. The method of claim 11, wherein the spring assembly is first spring assembly and the surgical tool further comprises a second spring assembly operatively coupled to a second input shaft, the method further comprising:
   providing a second constant torque force with the second spring assembly; and
   resisting rotation of the second input shaft with the second constant torque force and thereby preventing a second drive cable from slackening.

17. The method of claim 11, wherein resisting rotation of the input shaft with the constant torque force comprises resisting rotation of the input shaft in either angular direction with the constant torque force.

18. The method of claim 11, further comprising adjusting the constant torque force by adjusting a thickness of the constant force spring.

19. The method of claim 11, wherein a first end of the constant force spring is wrapped about the winder drum one or more times in a first angular direction, and a second end of the constant force spring is wrapped about the input shaft one or more times in a second angular direction opposite the first angular direction.

20. The method of claim 19, wherein the second end is coupled to a shaft extension that extends from the input shaft.

* * * * *